United States Patent [19]

Feder et al.

[11] Patent Number: 5,360,851

[45] Date of Patent: Nov. 1, 1994

[54] AQUEOUS SILICONE/(CO)POLYMER DISPERSIONS CROSSLINKABLE INTO ELASTOMERIC STATE

[75] Inventors: Michel Feder, Illfurth; Jean-Pierre Jaubert, Saint-Brice-Sous-Foret; Jean-Marie Pouchol, Lyons, all of France

[73] Assignee: Rhone-Poulenc Chimie, Courbevoie, France

[21] Appl. No.: 541,301

[22] Filed: Jun. 18, 1990

[30] Foreign Application Priority Data

Jun. 29, 1989 [FR] France .................... 89 09004

[51] Int. Cl.$^5$ .................................. C08K 5/42
[52] U.S. Cl. ............................ 524/157; 524/156; 524/161; 524/375; 524/378; 524/401; 524/405; 524/413; 524/423; 524/425; 524/430; 524/431; 524/432; 524/437; 524/442; 524/449; 524/450; 524/451; 524/506; 524/588
[58] Field of Search ............... 524/161, 262, 157, 588, 524/730, 745, 506, 437, 442, 449, 450, 451, 156, 375, 378, 401, 405, 413, 423, 425, 430, 431, 432

[56] References Cited

U.S. PATENT DOCUMENTS

| | | | |
|---|---|---|---|
| 4,288,356 | 9/1981 | Huebner et al. | 524/506 X |
| 4,433,007 | 2/1984 | Marwitz et al. | 524/506 X |
| 4,529,758 | 7/1985 | Traver | 524/506 X |
| 4,757,106 | 7/1988 | Mayer et al. | 524/506 X |
| 4,791,163 | 12/1988 | Traver et al. | 524/506 |
| 4,833,187 | 5/1989 | Sittenthaler et al. | 524/261 |
| 4,978,694 | 12/1990 | Vincent et al. | 524/506 X |

FOREIGN PATENT DOCUMENTS

| | | |
|---|---|---|
| 0049026 | 4/1982 | European Pat. Off. |
| 0117607 | 9/1984 | European Pat. Off. |
| 01177608 | 9/1984 | European Pat. Off. |

*Primary Examiner*—Judy M. Reddick
*Attorney, Agent, or Firm*—Burns, Doane, Swecker & Mathis

[57] ABSTRACT

Aqueous silicone dispersions crosslinkable into elastomeric state on removal of water therefrom under ambient conditions, well adapted, e.g., for the production of elastomeric silicone seals in the construction industry, include an oil-in-water base emulsion (A) of an $\alpha,\omega$-(dihydroxy)polydiorganosiloxane stabilized with at least one anionic or nonionic surface-active agent, or mixture thereof, (B) an aqueous latex of an organic (co)polymer having a particle size ranging from 0.01 to 0.5 $\mu$m and a solids content ranging from 20% to 70% by weight, (C) an effective crosslinking amount of at least one crosslinking agent, (D) an effective amount of at least one nonsiliceous filler material, and (E), optionally, a catalytically effective amount of a metal curing catalyst, such aqueous dispersions further having a solids content of at least 40% by weight.

25 Claims, No Drawings

AQUEOUS SILICONE/(CO)POLYMER DISPERSIONS CROSSLINKABLE INTO ELASTOMERIC STATE

BACKGROUND OF THE INVENTION

1. Field of the Invention

The present invention relates to novel aqueous dispersions based on a silicone and an organic polymer latex, such novel aqueous dispersions being crosslinkable into elastomeric state upon removal of water therefrom.

2. Description of the Prior Art

Silicone-based aqueous dispersions crosslinkable into elastomeric state on removal of water therefrom are known to this art. These comprise:

(a) an emulsion (A) of the oil-in-water type of an $\alpha,\omega$-(dihydroxy)polydiorganosiloxane, stabilized with an anionic and/or nonionic surfactant;
(b) a crosslinking agent;
(c) a nonsiliceous inorganic filler; and
(d) a curing catalyst.

The base emulsion contains a reactive silicone oil having silanol endgroups, which is generally polymerized in emulsion according to the technique described in U.S. Pat. Nos. 2,891,920, 3,294,725 and 3,360,491, namely, using an anionic surfactant which preferably also serves as the polymerization catalyst.

EP-A-327,321 describes an aqueous dispersion of the above type, in which the base emulsion is a mixture of a macroemulsion of a reactive silicone oil and a microemulsion of a reactive silicone oil having a particle size of less than 0.14 $\mu$m. A dispersion of this type presents the twin disadvantage of being costly and of crosslinking on evaporation of water into an elastomer exhibiting insufficient adhesiveness to substrates and/or mediocre mechanical properties.

In this general type of aqueous dispersion that crosslinks into elastomeric state on removal of water, the literature indicates the option of using a wide variety of crosslinking agents for the base emulsion, among which are:

(i) colloidal silica (U.S. Pat. Nos. 3,294,725 and 4,221,688);
(ii) sodium silicate (U.S. Pat. No. 4,244.849);
(iii) an amorphous silica powder (FR-A-2,463,163);
(iv) a microemulsion of a silsesquioxane resin (U.S. Pat. No. 3,355,406);
(v) a siliconate (EP-A-266,729, EP-A-332,544 and EP Application 89/4,200,567, filed Feb. 16, 1989 and assigned to the assignee hereof);
(vi) a reactive silicone resin of low molecular weight, containing alkoxy or acyloxy groups (U.S. Pat. No. 4,554,1870;
(vii) a silicone resin of high molecular weight, insoluble in toluene (EP-A-304,719);
(viii) a polyalkoxysilane, a polysilicate, a polyacyloxysilane or a polyketiminoxysilane (U.S. Pat. Nos. 3,294,725, 4,584,341, 4,618,642 and 4,608,412);
(ix) a polyamino- (or amido)silane (Application FR-A-89/01,654, filed Feb. 3, 1989 and assigned to the assignee hereof);
(x) a polyalkenoxysilane (Application FR-A-88/13,618, filed Oct. 11, 1988 and assigned to the assignee hereof);
(xi) a hydroxylated silicone resin containing, per molecule, at least two siloxy units selected from among those of the formulae: $R_3SiO_{0.5}$ (M), $R_2SiO$ (D), $RSiO_{1.5}$ (T) and $SiO_2$ (Q) (Application FR-A-88/11,609, filed Aug. 31, 1988 and also assigned to the assignee hereof).

These aqueous dispersions are typically catalyzed using a curing catalyst which is, preferably, a tin salt, and which may also be the combination of a tin salt and boric acid (U.S. Pat. No. 4,863,985).

However, these aqueous dispersions present many disadvantages, the most notable of which being:

(1) Insufficient storage stability;
(2) Mediocre adhesiveness to many substrates, in particular those employed in the construction industry (glass, concrete, metals, steel, aluminum, thick plastic coatings such as PVC, limestone, and the like);
(3) Paints prepared from these aqueous dispersions exhibit a binding power and a resistance to abrasion, in particular to wet abrasion, which may be insufficient;
(4) Elastomers produced from these aqueous dispersions on evaporation of water exhibit a very high shrinkage, associated with a modulus of elasticity (ME) and a tearing strength (TrS) which are too low for certain applications;
(5) Excessively high viscosity of silicone emulsions having high solids contents which are required for formulating filled aqueous dispersions of low volume extract.

Furthermore, organic (co)polymer latex aqueous dispersions, for example of alkyl (meth)acrylate and of vinyl esters of monocarboxylic acids, have long been used as paints to provide thin coatings or thick coatings, in particular in the construction industry for waterproofing facades and roofing.

These aqueous dispersions typically present the following disadvantages:

(1') The coating formed exhibits an insufficient permeability to gases and in particular to water vapor;
(2') The viscosity of the aqueous dispersion is too low and its film-forming capacity may be insufficient;
(3') The coatings obtained are too water-sensitive and insufficiently water-repellent;
(4') The coatings obtained are sensitive to actinic radiation and in particular to UV.

The patent literature has also described the combination of a silicone and an organic latex;

FR-A-2,526,033 and U.S. Pat. Nos. 4,012,355 and 2,739,910 describe the combination of a siliconate and an organic polymer latex;

DE-A-2,355,813 describes a system in which the siliconate may be replaced by a silicone resin emulsion; according to CH-A-61,842 both the siliconate and a silicone resin are associated with an acrylic acid copolymerizate.

None of these documents describes the further use of an emulsion of a silicone oil having silanol endgroups, of nonsiliceous filler and of curing catalysts.

EP-A-246,537 describes the preparation, in latex form, of a laminated elastomeric material of the following three elements:

(i) a core of crosslinked silicone rubber;
(ii) a first sheath of crosslinked acrylic rubber; and
(iii) a second sheath obtained by radical (co)polymerization of resin-forming monomers.

SUMMARY OF THE INVENTION

Accordingly, a major object of the present invention is the provision of novel aqueous dispersions of silicone and of an organic polymer latex which present the cumulative advantages of aqueous silicone dispersions and aqueous organic polymer dispersions, and even synergistic results in the case of certain desirable properties.

Another object of the present invention is the provision of novel dispersions of the above type which do not present the disadvantages inherent in dispersions of silicones alone or dispersions of organic polymers alone, or which novel dispersions conspicuously ameliorate said disadvantages, which is acceptable in the majority of the uses of such dispersions.

Yet another object of this invention is the provision of novel dispersions of the above type which, after crosslinking, optionally exhibit the following properties at the same time:

(1) A storage stability of at least six months, preferably at least one year;

(2) A viscosity of the unfilled material and of the material packaged in a cartridge which is suitable even in the event of aqueous dispersions which have a high solids content of more than 75%, these dispersions producing elastomers of relatively low modulus;

(3) A satisfactory adhesiveness to the widest variety of substrates, e.g., stone, concrete, mortar, metals, steel, aluminum, fibro-cement, enamels, ceramics and plastics such as PVC;

(4) A suitable viscosity, endowing them with an extrudability from the packaging cartridge and a suitable film-forming capacity;

(5) A suitable resistance to abrasion, in particular to wet abrasion, to atmospheric moisture and to actinic radiations (visible light, UV);

(6) Good permeability to gases and to water vapor;

(7) Satisfactory mechanical properties, in particular as regards modulus of elasticity and tear strength;

(8) A satisfactory water-repellency.

Briefly, the present invention features aqueous dispersions based on a silicone that are crosslinkable into elastomeric state upon removal of water therefrom under ambient conditions, comprising, by weight:

(A) 100 parts of an oil-in-water emulsion of an $\alpha,\omega$-(dihydroxy)polydiorganosiloxane, stabilized with at least one surface-active agent selected from among the anionic and nonionic surface-active agents and mixtures thereof;

(B) 2 to 80, preferably 3 to 40, parts of an aqueous dispersion of an organic (co)polymer which has a particle size ranging from 0.07 to 0.5 $\mu$m, preferably from 0.05 to 0.2 $\mu$m, and a solids content ranging from 20% to 70% by weight;

(C) an effective amount of at least one crosslinking agent;

(D) 5 to 200, preferably 50 to 150, parts of a nonsiliceous inorganic filler;

(E) optionally, 0.01 to 3 parts by weight of a metal curing catalyst, and said dispersions having a dry solids content of at least 40%.

DETAILED DESCRIPTION OF THE PREFERRED EMBODIMENTS OF THE INVENTION

More particularly according to the present invention, the final aqueous dispersion is prepared simply by thoroughly mixing all of the constituents thereof, resulting in a homogeneous dispersion which is stable in storage in the absence of air.

The Emulsions (A)

The $\alpha,\omega$-(dihydroxy)polydiorganosiloxanes must have a viscosity of at least 100 mPa.s at 25° C., preferably of at least 50,000 mPa.s.

Indeed, it is in the case of viscosities above 50,000 mPa.s that an elastomer is produced which exhibits a combination of suitable mechanical properties, in particular with regard to Shore A hardness and elongation.

In addition, the higher the viscosity, the more the mechanical properties are preserved when the elastomer is aged.

According to the present invention, the preferred viscosities range from 50,000 to 1,500,000 mPa.s at 25° C.

The organic radicals of the $\alpha,\omega$-(dihydroxy)polydiorganopolysiloxanes are monovalent hydrocarbon radicals having up to 6 carbon atoms, optionally substituted by cyano or fluoro groups. The radicals which are typically employed, because of their presence in the commercially available siloxanes, are methyl, ethyl, propyl, phenyl, vinyl and. 3,3,3-trifluoropropyl radicals. At least 80% of the number of these radicals are generally methyl radicals.

In a preferred embodiment of the present invention, $\alpha,\omega$-(dihydroxy)polydiorganopolysiloxanes are used that have been prepared by the anionic polymerization technique described in the above U.S. Pat. No. 2,891,920 and especially U.S. Pat. No. 3,294,725, hereby incorporated by reference. The polymer obtained is stabilized anionically with a surface-active agent which, according to U.S. Pat. No. 3,294,725, is preferably the alkali metal salt of an aromatic hydrocarbon sulfonic acid, the free acid also serving as the polymerization catalyst.

The preferred catalyst and surface-active agent are dodecylbenzenesulfonic acid and its alkali metal salts, in particular its sodium salt. Other anionic or nonionic surface-active agents may optionally be added. However, this addition is not necessary because, in accordance with U.S. Pat. No. 3,294,725, the amount of anionic surface-active agent resulting from the neutralization of the sulfonic acid is sufficient to stabilize the polymer emulsion. This amount if typically less than 3%, preferably 1.5% of the weight of the emulsion.

This emulsion polymerization process is of particular interest because it permits the direct preparation of the emulsion (A). Moreover, this process permits the option of easily obtaining $\alpha,\omega$-(dihydroxy)polydiorganosiloxane emulsions (A) of very high viscosity.

To prepare the emulsion (A), it is also possible to begin with already polymerized $\alpha,\omega$-(dihydroxy)-polydiorganosiloxane and then to convert it into an aqueous emulsion, stabilizing the emulsions with an anionic and/or nonionic surface-active agent according to technique which is well known to this art and abundantly described in the literature (see, for example, FR-A-2,064,563, FR-A-2,094,322, FR-A-2,114,230 and EP-A-169,098.

According to this process, the α,ω-(dihydroxy)-polydiorganosiloxane polymers are mixed with the anionic or nonionic surface-active agent simply by stirring, it being possible for the latter material to be in aqueous solution, then to add water, if necessary, and to convert the entire mass into a fine and homogeneous emulsion by passing it through a conventional colloid mill.

The millbase obtained is subsequently diluted with an appropriate amount of water and a storage-stable emulsion (A) stabilized with an anionic or nonionic surface-active agent is thus obtained.

The amount of anionic and nonionic surface-active agent which can be employed is that commonly used in the emulsification process, in particular those described in the aforementioned patents and in U.S. Pat. No. 2,891,920.

The anionic surface-active agents which are preferred according to the present invention are the alkali metal salts of an aromatic hydrocarbon sulfonic acid and the preferred nonionic surface-active agents are polyoxyethylenated alkylphenols. These nonionic surface-active agents are, of course, the same as those which can optionally be added to the emulsions (A) produced by emulsion polymerization, as indicated above.

The emulsion (A) prepared by emulsion polymerization or by emulsifying the silicone polymer is in the form of an oil-in-water emulsion and preferably has a solids content of at least 40% by weight.

The Dispersion (B)

This is a "latex" formulated from an aqueous dispersion of polymer particles resulting from conventional processes of emulsion (co)polymerization of polymerizable organic monomers. These organic monomers are preferably selected from among:

(a) Alkyl (meth)acrylates, the alkyl moiety of which preferably has from 1 to 18 carbon atoms, in particular methyl acrylate, ethyl acrylate, propyl acrylate, n-butyl acrylate, isobutyl acrylate, amyl acrylate, lauryl acrylate, isoamyl acrylate, 2-ethylhexyl acrylate, octyl acrylate, methyl methacrylate, chloroethyl methacrylate, butyl methacrylate, 3,3-dimethylbutyl methacrylate, ethyl methacrylate, isobutyl methacrylate, isopropyl methacrylate, phenyl methacrylate, butyl chloroacrylate, methyl chloroacrylate, ethyl chloroacrylate, isopropyl chloroacrylate and cyclohexyl chloroacrylate;

(b) α,β-Ethylenically unsaturated esters of monocarboxylic acids, the acidic moiety of which is nonpolymerizable and the unsaturated moiety preferably has from 2 to 14 carbon atoms and the acidic moiety from 2 to 12 carbon atoms, in particular vinyl acetate, vinyl propionate, vinyl butyrate, allyl acetate, vinyl versatate ® (registered trademark for esters of $C_9$–$C_{11}$ α-branched acids), vinyl laurate, vinyl benzoate, vinyl trimethylacetate, vinyl pivalate and vinyl trichloroacetate;

(c) The esters and half-esters of α,β-ethylenically unsaturated polycarboxylic acids having from 4 to 24 carbon atoms, in particular dimethyl fumarate, diethyl maleate, methyl ethyl fumarate and 2-ethylhexyl fumarate;

(d) Vinyl halides, in particular vinyl chloride, vinyl fluoride, vinylidene chloride and vinylidene fluoride;

(e) Vinylaromatic compounds preferably having not more than 24 carbon atoms and selected in particular from among styrene, α-methylstyrene, 4-methylstyrene, 2-methylstyrene, 3-methylstyrene, 4-methoxystyrene, 2-hydroxymethylstyrene, 4-ethylstyrene, 4-ethoxystyrene, 3,4-dimethylstyrene, 2-chlorostyrene, 3-chlorostyrene, 4-chloro-3-methylstyrene, 4-tert-butylstyrene, 4-dichlorostyrene, 2,6-dichlorostyrene, 2,5-difluorostyrene and 1-vinylnaphthalene.

(f) Conjugated aliphatic dienes preferably having from 3 to 12 carbon atoms, in particular 1,3-butadiene, isoprene and 2-chloro-1,3-butadiene;

(g) α,β-ethylenically unsaturated nitriles preferably having from 3 to 6 carbon atoms, such as acrylonitrile and methacrylonitrile.

Polystyrene latices and polyvinylacetate latices are particularly representative homopolymer latices.

Dispersions (B) which can be used according to the present invention are, for example, those containing a copolymer obtained by copolymerization:

(i) of a monomer (a) and of a monomer (b), such as copolymers of the vinyl acetate/alkyl acrylate type;

(ii) of a monomer (a), of a monomer (b) and of a monomer (c), such as, for example, a terpolymer of the acetate/acrylate/maleate type;

(iii) of a monomer (b), of a monomer (d) and of an olefinic monomer, such as, for example, the acetate/vinyl chloride/ethylene terpolymer;

(iv) of a monomer (e) and of a monomer (a), among which styrene/alkyl acrylate copolymers in which the styrene/alkyl acrylate weight ratio ranges from 30/70 to 70/30 are very particularly representative;

(v) of a monomer (e) and of an α,β-ethylenically unsaturated carboxylic acid preferably having from 4 to 12 carbon atoms, including mono- and polycarboxylic acids such as (meth)acrylic acids, itaconic acid, maleic acid, fumaric acid, such as the styrene/methacrylic acid copolymer;

(vi) of a monomer (e), of an α,β-ethylenically unsaturated carboxylic acid indicated above and of a monomer (g), such as the styrene/acrylonitrile/itaconic acid copolymers;

(vii) of a monomer (e) and of a monomer (f).

In addition to the principal monomers (e) to (g) indicated above, it is possible to copolymerize certain of these principal monomers with up to 15% by weight of other monomers that are ionic in character, in particular:

(1) an α,β-ethylenically unsaturated carboxylic acid monomer indicated above, including mono- and polycarboxylic acids (acrylic, methacrylic, maleic, itaconic, fumaric and similar acids);

(2) an ethylenic monomer containing secondary, tertiary or quaternized amine groups (vinylpyridines, diethylaminoethyl methacrylate, etc.);

(3) a sulfonated ethylenic monomer (vinyl sulfonate, styrenesulfonate, etc.);

(4) a zwitterionic ethylenic monomer (sulfopropyl(dimethylaminopropyl) acrylate); or nonionic in character, in particular:

(5) amides of unsaturated carboxylic acids (acrylamide, methacrylamide, etc.);

(6) esters of (meth)acrylates and of polyhydroxypropyl or polyhydroxyethylated alcohols.

The stabilization of the polymer particles within the aqueous dispersions is ensured either by the aforesaid comonomers of ionic or nonionic character, or by emulsifiers (surfactants), which are preferably nonionic, such as polyethoxylated fatty alcohols, polyethoxylated alkylphenols and polyethoxylated fatty acids, or anionic such as alkylsulfates, alkylsulfonates or alkylarylsulfonates (in particular dodecylbenzenesulfonate and dialkylsulfosuccinates).

The above aqueous dispersions of organic polymers are abundantly described in the literature. According to this invention, they advantageously have a solids content which generally ranges from 20% to 70% by weight and a particle size ranging from 0.01 to 0.5 μm, preferably from 0.05 to 0.30 μm.

The aqueous dispersions (B) in which the particle size is small, below approximately 0.15 μm, make it possible, in fact, to increase the solids content of the aqueous dispersions in a cartridge while preserving a suitable viscosity. After evaporation of water, these final aqueous dispersions produce elastomers of low modulus and of lower volume shrinkage.

In order to produce an elastomer of this type, the aqueous dispersion according to the invention, resulting from the mixing of the emulsion (A) and of the dispersion (B), preferably has:

(i) a "twin population" particle size distribution, namely, a first population of particles preferably originating essentially from the dispersion (B) whose particle size ranges from approximately 0.01 μm to 0.15 μm, preferably 0.10 μm, and a second population of particles originating preferably essentially from the emulsion (A) and exhibiting a particle size ranging from 0.15 μm to 100 μm, generally from 0.20 μm to 5 μm;

(ii) a solids content of more than 60% by weight, preferably more than 70% by weight;

(iii) a viscosity of less than 50,000 mPa.s at 25° C., measured at a shear rate of 1 s$^{-1}$, prior to the incorporation of the fillers (D), such as to provide a final dispersion which can easily be extruded from the storage cartridge.

To prepare such twin-population dispersions, it is particularly advantageous to carry out the emulsion polymerization of the emulsion (A) in the presence of the dispersion (B) in the case where this dispersion (B) has a low solids content of, for example, from 20% to 40% by weight.

Film-forming or nonfilm-forming latices (dispersion B) may be employed according to the present invention.

By "film-forming" latex is intended a latex whose polymer particles coalesce to form a film at the temperature of application of the final dispersion. This temperature can range from 5° to 45° C. It is generally about 20° C. Conversely, by "non-film-forming" latices are intended those whose polymer particles remain as discrete entities in the final material and do not coalesce at the temperature of application of the final dispersion, i.e., during the evaporation of water and its conversion into elastomer.

The preparation of film-forming or nonfilm-forming latices (see, in particular, U.S. Pat. No. 3,819,557 in the case of nonfilm-forming latices) is well known to this art and entails monomer(s) selection, adapting the emulsion polymerization process and optionally adding a solvent. To obtain a nonfilm-forming latex, it is generally sufficient for the organic (co)polymer to have a glass transition temperature which is higher than the temperature of formation of the elastomer from the final dispersion, namely, higher than 45° C. However, the use of a film-forming latex is preferred, because the end result is an elastomer which has improved flexibility properties.

The Crosslinking Agent (C)

During the crosslinking of the aqueous dispersion, the crosslinking agent permits reticulation of the elastomeric lattice by polycondensation reactions between the reactive groups of the crosslinking agent and the silanol endgroups of the silicone oil of the emulsion (A).

As described in the patents indicated above, where exist many different crosslinking agents which can be employed by themselves or mixed. The amounts of crosslinking agents to be introduced into the aqueous dispersion depend precisely on the nature of the crosslinking agent employed.

By "effective amount" of (C) is intended an amount which enables production of an elastomer.

Exemplary crosslinking agents are indicated below, with the recommended amounts in the final dispersion, such amounts being expressed in parts by weight per 100 parts of emulsion (A):

(i) 0.1 to 10 parts of colloidal silica;
(ii) 0.5 to 10 parts of sodium silicate;
(iii) 1 to 15 parts of silica powder selected from pyrogenic or fumed silicas and precipitated silicas;
(iv) 0.1 to 15 parts, preferably 1 to 10 parts of an organosiliconate;
(v) 1 to 100 parts of a silsesquioxane resign microemulsion according to the combined teachings of U.S. Pat. Nos. 3,355,406 and 3,433,780;
(vi) 5 to 100 parts of a reactive silicone resin of low molecular weight, containing alkoxy and acyloxy groups;
(vii) 5 to 100 parts of a silicone resin of high molecular weight, insoluble in toluene;
(viii) 5 to 100 parts of a hydroxylated silicone resin containing, per molecule, at least 2 different units selected from those of the formulae: $R_3SiO_{0.5}$ (M), $R_2SiO$ (D), $RSiO_{1.5}$ (T) and $SiO_2$ (Q), R preferably being a $C_1$-$C_6$ alkyl, vinyl and 3,3,3-trifluoropropyl radical, and having a weight content of hydroxyl groups of from 0.1% to 10%; among these resins, which are introduced as such or in the form of aqueous emulsions, representative are MQ, MDQ, TD and MTD resins;
(ix) 1 to 20 parts of a silane of the formula:

in which R is a monovalent organic radical, in particular methyl or vinyl a is 1 or 0, and X is a condensable and/or hydrolyzable group preferably selected from among alkoxy, acyloxy, ketiminoxy, alkylamino, amido and alkenyloxy groups.

In the case where X is alkoxy, it is desirable to add 2-amino-2-methylpropanol as stabilizer, according to EP-A-259,734.

The Nonsiliceous Inorganic Filler (D)

Another constituent of the dispersion according to the invention is 5 to 200, preferably 10 to 150, parts by weight of an inorganic semireinforcing or packing filler (D).

The fillers (D) advantageously have a particle size which typically ranges from 0.001 to 300 μm and a BET surface area of less than 100 m$^2$/g.

Exemplary fillers (D) which can be employed by themselves or mixed are carbon black, titanium dioxide, aluminum oxide, hydrated alumina, expanded vermiculite, unexpanded vermiculite, hydrated borax, calcium carbonate, zinc oxide, mica, talc, iron oxide, barium sulfate and slaked lime. Precipitated calcium carbonate having a mean particle diameter of less than 0.1 μm is an example of a preferred nonsiliceous inorganic filler (D).

These fillers (D) are introduced into the emulsion in the form of dry powder, for example simply by mixing.

According to an alternative embodiment of the invention, it has been found that if the filler (D) consists essentially only of a filler selected from among hydrated alumina, expanded vermiculite, unexpanded vermiculite and hydrated borax in an amount of 5 to 200, preferably of 50 to 150, parts per 100 parts of emulsion (A), then an elastomer is produced which has a particularly high flame resistance which cannot be attained from the other above-mentioned categories of filler (D), in particular with aluminum oxide or unhydrated alumina. Ceramic or aramid fibers can also be incorporated, according to EP-A-212,827.

In another alternative embodiment, it is possible to incorporate, per 100 parts by weight of the emulsion (A), a siliceous additive (F) selected from sodium silicate (0.3 to 30 parts), and a reinforcing or semireinforcing siliceous filler (1 to 100 parts), insofar, of course, as this siliceous additive has not already been selected as the crosslinking agent (C).

These siliceous fillers are selected from among colloidal silica, pyrogenic and precipitated silica powders, or mixtures thereof. Pyrogenic silica is preferred. Semireinforcing siliceous fillers, such as diatomaceous earths or ground quartz can, however, also be employed.

The sum of the parts of (D)+(F) must be less than 350 parts by weight per 100 parts by weight of emulsion (A).

The pyrogenic and precipitated silica powders are well known to this art; in particular, they are employed as fillers in silicone elastomer compositions heat-vulcanizable into a silicone rubber. These powders have a mean particle size which is typically less than 0.1 μm and a BET specific surface area of more than 50 $m^2/g$, preferably ranging from 150 to 350 $m^2/g$.

The incorporation of this siliceous additive (F) in the emulsion (A) by any suitable means, in particular by stirring, considerably increases the viscosity of the emulsion (A), which is then pasty in nature.

Indeed, it has now been found according to the present invention that the addition of this siliceous additive (F) is sufficient to impart a more or less pronounced "thixotropic" nature to the emulsion. The emulsion extracted, for example from a storage cartridge, adheres without flowing, even on a vertical substrate, and cures into elastomeric state on evaporation of water therefrom at room (ambient) temperature. A nonflowing emulsion can also be obtained by using as filler (D) calcium carbonate, the mean particle diameter of which is less than 0.1 μm.

The Metal Curing Catalyst (E)

The compound (E) is optional, in particular in the case of certain crosslinking agents (C) such as a siliconate, but it is preferred to use the catalyst (E) according to the present invention.

The metal curing catalyst compounds (E) are advantageously carboxylic acid salts and halides of metals selected from among lead, zinc, zirconium, titanium, iron, tin, barium, calcium and manganese.

The constituent (E) is preferably a tin catalyst compound, typically an organotin salt, preferably introduced in the form of an aqueous emulsion. The organotin salts which can thus be used are described, in particular, in the text by Noll, *Chemistry and Technology of Silicones*, Academic Press, page 337 (1968).

It is also possible to use the product of reaction of an alkyl silicate or of an alkyl trialkoxysilane with dibutyltin diacetate, as described in BE-A-842,305.

The preferred tin salts are tin bischelates (EP-A-147,323 and EP-A-235,049), diorganotin dicarboxylates and in particular dibutyl- or dioctyltin diversatates (GB-A-1,289,900), dibutyl- or dioctyltin diacetate, and dibutyl- or dioctyltin dilaurate. From 0.01 to 3, preferably from 0.05 to 2, parts by weight of organotin salt are employed per 100 parts by weight of (A).

The aqueous dispersions according to the invention may additionally comprise the usual additives and adjuvants such as, especially, fungicides, antifoams, antifreezes such as ethylene glycol and propylene glycol, and thixotropic agents such as carboxymethyl cellulose, xanthan gum and polyvinyl alcohol, dispersing agents (phosphates) or plasticizers (unreactive silicone oils or organic plasticizers such as alkylbenzenes having a molecular weight of more than 200).

To prepare the aqueous dispersions according to the invention, it is advantageous to add to the emulsion (A) at room temperature, with stirring, first the dispersion (B) and then the crosslinking agent (C), optionally in the form of a dispersion or of an aqueous emulsion, then the metal curing catalyst (E) and lastly the nonsiliceous inorganic filler (D) and, optionally, the siliceous additive (F).

The pH of the aqueous dispersion may be acidic, neutral or basic. Nevertheless, it is advantageous to adjust the pH of the dispersion to a value ranging from 8 to 13 by means of a strong inorganic or organic base (triethanolamine, sodium hydroxide, potassium hydroxide).

The final dispersion obtained is homogenized and is then degassed and subsequently packaged in a container or package which is sealed against atmospheric oxygen and water vapor.

The constituents (A), (B), (C), (D) and (E) and optionally (F) are mixed in such amounts that the final emulsion has a solids content of more than 40%, preferably more than 60%, but generally less than 90%. The preferred pH range is from 8 to 13.

The dispersions according to the invention can be employed as a paint capable of being crosslinked in a thin layer. Such paints preferably have a solids content ranging from 40% to 70%.

To determine the solids content, 2 g of dispersion are placed in an aluminum weighing dish and this is heated for one hour at 150° C. in an oven provided with air circulation. After cooling, the dish is weighed again and the remaining material is determined as a percentage of the initial 2 g, which represents the solids content.

In a preferred embodiment, after preparation thereof, the dispersion according to the invention is subjected to a stage of aging at room temperature, for from a few hours to several days.

This aging stage simply entails permitting the dispersion to stand protected against atmospheric oxygen before it is employed.

The dispersions according to the invention can be employed for the production of silicone elastomer seals, in particular for the construction industry and as water-repellent coatings for structural surfaces in contact with inclement weather, in a proportion, for example, of 20 to 100 g of dispersion per $m^2$ of surface to be coated.

These dispersions can also be employed for coating various pharmaceutical or plant-protection active substances formulated in a solid form (pastilles, tablets, pills and the like), for coating cork stoppers employed for sealing bottles of wines and of spirits, for coating kitchenware and, in general, articles in contact with foodstuffs (for example bread molds).

Known coating techniques can be employed, in particular techniques of coating with a brush and by dipping (by immersion), spraying techniques, fluidized bed coating techniques and immersion coating techniques.

In the case of coatings for cork stoppers, a recommended technique is the dip-coating technique, which entails immersing the stoppers in the dispersion, which wets the surface of the stopper, and then evaporating off the water.

The coating obtained represents 20 to 50 mg of elastomer per 100 cm$^2$ of stopper surface. This layer makes it easier for the stopper to slide in the neck of the bottle during the bottling and prevents "running", namely, leakages of liquid between the neck and the stopper.

The dispersions according to the invention can also be employed in cosmetology in the case where their pH is consistent with the particular intended application.

Thus, the dispersions can be incorporated into cosmetic compositions for the treatment of hair, especially for permanent waving with a view to creating a porous elastomeric film on the strands of hair, according to EP-A-240,349 and EP-A-240,350, hereby incorporated by reference.

The dispersions can also be employed in face mask cream compositions and also for producing dermocopies (reproduction of the skin in relief).

Finally, the dispersions according to the invention can be used as hair-removal compositions as described in U.S. Pat. No. 4,734,099, hereby also incorporated by reference.

In order to further illustrate the present invention and the advantages thereof, the following specific examples are given, it being understood that same are intended only as illustrative and in nowise limitative.

EXAMPLE 1

An emulsion (A) was prepared by polymerizing 1,000 g of an α,ω-(dihydroxy)polydimethylsiloxane oil having a viscosity of 100 mPa.s at 25° C. in the presence of 30 g of dodecylbenzenesulfonic acid and 50 g of Cemulsol ® ON 10/20, marketed by Rhone-Poulenc, which is a nonionic surfactant, namely, a polyoxyalkylenated compound containing approximately 10 ethylene oxide units and 20 propylene oxide units.

The emulsion polymerization was terminated by neutralizing the catalyst with 14.5 g of triethanolamine when the viscosity of the oil reached 55,000 mPa.s at 25° C.

The resulting emulsion (A) had a solids content of 60%.

In the case of each additive, the following were incorporated under stirring for 10 minutes in 131 parts of emulsion (A):
  (i) 40 parts of a styrene/butyl acrylate latex forming a film at room temperature, marketed by Rhone-Poulenc under the trademark Rhodopas ® DS910, and having the following characteristics:
     Solids content: 50%
     pH : 8
     Brookfield viscosity (500 revolutions/min) 4,500 mPa.s
     Minimum film formation temperature : 16° C.
     Particle diameter: 0.1 μm
     Density of the dispersion: 1.032 g/cm$^3$
     Density of the polymer: 1.068 g/cm$^3$
     Refractive index of the polymer at 25° C.: 1.532;
  (ii) 7 parts of an aqueous solution of potassium methylsiliconate having a solids content of 40%;
  (iii) 2.6 parts of an aqueous emulsion containing 37% by weight of di-n-octyltin dilaurate;
  (iv) 80 parts of precipitated CaCO$_3$ having a mean particle size of 70 nanometers.

The final dispersion had a solids content of 70% and a pH of 9.

After 7 days of storage, the dispersion was spread with a doctor blade into a 2-mm thick film, which was permitted to dry at room temperature (20° C.) for 10 days.

The following average mechanical properties were measured on a first batch of dried films:
  (a) the Shore A hardness (SAH) according to ASTM Standard D-2240;
  (b) the tensile strength (TS) according to AFNOR Standard T-46 002, corresponding to ASTM Standard D 412, in MPa;
  (c) the elongation at break (EB) in % according to AFNOR Standard T 46 002;
  (d) the elasticity modulus (EM) at 100% elongation according to AFNOR Standard T 46 002, in MPa.

The mechanical properties obtained are reported in Table 1 below.

To assess adhesiveness, a 4-mm thick bead of aqueous dispersion was deposited onto a glass or concrete support. After 12 days, the adhesiveness of the elastomer formed was assessed by pulling the bead by hand.

The adhesions were qualified in three ways:
  (1) good adhesiveness when the bead could not be stripped from its support (indicated as ++);
  (2) average adhesiveness when the bead is stripped with difficulty and over small surfaces (indicated as +);
  (3) absence of adhesiveness when the bead is stripped easily (indicated as 0).

The assessments of the adhesion are reported in Table 1 below.

COMPARATIVE EXAMPLE 2

The procedure of Example 1 was repeated exactly, except that 171 parts of emulsion (A) were used without incorporating the 40 parts of organic latex. The final dispersion had a solids content of 72% and a pH of 9.

The mechanical properties and the assessments of adhesion are reported in Table 1 below.

It will be seen that the compositions of the invention exhibited improved mechanical and adhesion properties when compared with the control of Comparative Example 2.

TABLE 1

|  | EXAMPLE 1 Parts by weight | COMPARATIVE EXAMPLE 2 Parts by weight |
|---|---|---|
| Emulsion (A) | 131 | 171 |
| Organic latex | 40 | 0 |
| Aqueous solution containing 40% of potassium methylsiliconate | 7 | 7 |
| Dioctyltin dilaurate emulsion | 2.6 | 2.6 |
| Precipitated CaCO$_3$ (φ ≃ 70 nm) | 80 | 80 |
| pH | 9 | 9 |
| Hardness (Shore A) | 40 | 23 |
| TS (MPa) | 1.23 | 1.02 |
| EB (%) | 381 | 639 |

TABLE 1-continued

| | EXAMPLE 1<br>Parts by weight | COMPARATIVE<br>EXAMPLE 2<br>Parts by weight |
|---|---|---|
| 100% modulus (MPa) | 0.90 | 0.31 |
| Adhesiveness to: | | |
| glass: | + | + |
| concrete: | ++ | + |

EXAMPLE 3

Preparation of two silicone dispersions for paints ($a_1$) and ($a_2$):

3.$a_1$.- Preparation of tin-catalyzed dispersion ($a_1$)

An emulsion (A) was prepared by polymerizing 1,000 g of an $\alpha,\omega$-(dihydroxy)polydimethylsiloxane oil having a viscosity of 100 mPa.s at 25° C. in the presence of 30 g of dodecylbenzenesulfonic acid and 50 g of Cemulsol® ON 10/20, which is a nonionic surfactant, namely, a polyoxyalkylenated compound containing 10 ethylene oxide units and 20 propylene oxide units.

The emulsion polymerization was terminated by neutralizing the catalyst with 14.5 g of triethanolamine when the viscosity of the oil reached 900,000 mPa.s at 25° C.

To 171 parts of the emulsion (A) were added 7 parts of a solution of potassium methylsiliconate having a solids content of 40% and 2.6 parts of aqueous emulsion containing 37% by weight of di-n-octyltin dilaurate. The dispersion ($a_1$) was thus obtained.

3.$a_2$.- Preparation of catalyzed dispersion ($a_2$)

The procedure described in 3.$a_1$. was repeated exactly, except that the 2.6 parts of tin emulsion were not added.

EXAMPLE 4

Preparation of a tin-catalyzed silicone/styrene/acrylic latex mixed paint:

The following constituents were introduced in succession into a kneader:
(i) Water: 10 parts
(ii) Sodium hexametaphosphate in aqueous solution at a concentration of 10%: 2 parts
(iii) Xanthan gum marketed by Rhone-Poulenc under the trademark Rhodopol® 23 in aqueous solution at a concentration of 0.4%: 5 parts
(iv) Titanium dioxide marketed by Rhone-Poulenc under the trademark Rex®: 12.5 parts
(v) Talc marketed by "Les Talcs de Luzenac" under the trademark 2OMO®: 3.6 parts
(vi) Calcium carbonate marketed by Omya under the trademark Durcal®5: 14.5 parts
(vii) Barium sulfate marketed by SCZ under the trademark Rutenia®: 7 parts
(viii) Dispersion ($a_1$): 19.6 parts
(ix) Styrene/acrylic latex (Rhodopas® DS910 employed in Example 1): 15.5 parts
(x) Polyacrylate thickener: 2 parts Finally, there was added:
(xi) Water: 7.9 parts A tin-catalyzed silicone/styrene/acrylic latex mixed paint was thus obtained.

COMPARATIVE EXAMPLE 5c

Preparation of a pure silicone paint:

The procedure of Example 4 was repeated exactly except that the 15.5 parts of styrene/acrylic latex were replaced with 13.4 additional parts of silicone dispersion ($a_1$).

EXAMPLE 6

Preparation of a silicone/styrene/acrylic latex mixed paint not catalyzed with tin:

To prepare this paint, the procedure of Example 4 was repeated exactly, except that the 19.6 parts of ($a_1$) were replaced with 19.6 parts of ($a_2$).

COMPARATIVE EXAMPLE 7C

Preparation of a pure silicone paint not catalyzed with tin:

To prepare this paint, the procedure of Example 6 was repeated exactly, except that the 15.5 parts of styrene/acrylic latex were replaced with 13.4 additional parts of silicone dispersion ($a_2$).

COMPARATIVE EXAMPLE 8C

Preparation of a pure styrene/acrylic latex paint:

To prepare this paint, the procedure of Example 6 was repeated exactly, except that the 19.6 parts of dispersion ($a_1$) were replaced with 22.5 additional parts of styrene/acrylic latex DS910.

EXAMPLE 9

Evaluation of the water vapor permeability of dried paint films prepared according to the procedure of Example 4, 5C, 6, 7C and 8C:

Measurements of porosity to water vapor were carried out by according to the procedure of AFNOR Standard NF T30 704.

These paints (having a weight ratio of pigment+fillers to binder of approximately 2/1) were applied onto a fibro-cement substrate. The weight loss of a glass dish (80 mm height, 170 mm diameter) containing a water reserve and sealed by the painted test specimen was measured every 24 hours. The entire assembly was placed in an enclosure maintained at 23° C.

The respective porosities P, expressed in $g/m^2$ per 7 days of test, are reported in Table 2 below.

From Table 2 below, it will be seen that the paints according to the invention have a porosity close to the pure silicone paint 7C.

Evaluation of the wet abrasion behavior of the paints prepared according to the procedure of Examples 4, 5C, 6, 7C and 8C:

This wet abrasion behavior was evaluated according to DIN Standard 53778, by rubbing a paint film provided with certain soiling and scrubbed with a brush using a back-and-forth motion under certain conditions.

The wet abrasion behavior was assessed as the number N of cycles performed by the brush to reduce the thickness of the coat of paint by 50%.

The results obtained are reported in Table 2 below, from which it will be seen that the paints according to the invention exhibited a wet abrasion resistance which was much superior to the all-silicone paints of Examples 5C and 7C.

TABLE 2

| EXAMPLE | 4 | 5C | 6 | 7C | 8C |
|---|---|---|---|---|---|
| POROSITY $g/m^2$ | 290 | 350 | 310 | 370 | 210 |
| N | 900 | 150 | 500 | 50 | >10,000 |

EXAMPLE 10

An emulsion (A) was prepared by polymerizing 1,000 g of an α,ω-(dihydroxy)polydimethylsiloxane oil having a viscosity of 100 mPa.s at 25° C. in the presence of 30 g of dodecylbenzenesulfonic acid and 50 g of Cemulsol ® ON 10/20, which is a nonionic surfactant, namely, a polyoxyalkylenated compound with approximately 10 ethylene oxide units and 20 propylene oxide units.

The emulsion polymerization was terminated by neutralizing the catalyst with 14.5 g of triethanolamine when the viscosity of the oil reached 300,000 mPa.s at 25° C.

The emulsion (A) obtained had a solids content of 60%.

In the case of each additive, the following constituents were incorporated under stirring for 10 minutes, in 158 parts of emulsion (A):

(i) 7 parts of polyvinyl acetate emulsion forming a film at a temperature above 15° C., marketed by Rhone-Poulenc under the trademark Rhodopas AO15, which had the following characteristics:
Solids content : 62%
Viscosity at 25° C.: 3,500 mPa.s
Diameter of twin-population particles: 0.1–0.3 μm and 1.5–3 μm;

(ii) 2.2 parts of 50% strength potassium hydroxide solution;

(iii) 7 parts of a hydroxylated silicone resin introduced as such, containing 2.2% by weight of hydroxyl groups, comprising 70% by weight of $CH_3SiO_{1.5}$ units and 30% by weight of $(CH_3)_2SiO$ units. This resin was soluble in toluene and had a molecular weight of approximately 1,300 and a $CH_3/Si$ molar ratio = 1.77;

(iv) 2.6 parts of an aqueous emulsion containing 37% by weight of di-n-octyltin dilaurate;

(v) 100 parts of precipitated $CaCO_3$ having a mean particle size of 70 nanometers.

The final mixture was homogenized for another 30 minutes at a reduced pressure of 1.33 kPa.

The final dispersion had a solids content of 75% and a pH of 9.

The mechanical properties and the quality of the adhesions were measured according to the method described in Example 1, together with the flow threshold in Pa, measured with a Carrimed ® viscometer.

The results obtained are reported in Table 3 below.

COMPARATIVE EXAMPLE 11

The procedure of Example 10 was repeated exactly, except that the 7 parts of polyvinyl alcohol emulsions were not incorporated. The final dispersion had a solids content of 76% and pH of 9.

The mechanical properties and the assessments of adhesion are reported in Table 3 below.

EXAMPLE 12 AND 13

The procedure of Example 10 was repeated, except that 20 and 40 parts of polyvinyl alcohol emulsion were introduced, respectively.

The results obtained are reported in Table 3 below.

TABLE 3

|  | Comparative Example 11 parts by weight | Example 10 parts by weight | Example 12 parts by weight | Example 13 parts by weight |
|---|---|---|---|---|
| Emulsion (A) | 158 | 158 | 158 | 158 |

TABLE 3-continued

|  | Comparative Example 11 parts by weight | Example 10 parts by weight | Example 12 parts by weight | Example 13 parts by weight |
|---|---|---|---|---|
| Rhodopas AO15 | 0 | 7 | 20 | 40 |
| Silicone resin | 7 | 7 | 7 | 7 |
| Dioctyltin dilaurate emulsion | 2.6 | 2.6 | 2.6 | 2.6 |
| Precipitated $CaCO_3$ (φ ≃ 70 nm) | 100 | 40 | 100 | 100 |
| KOH (50%) | 2.2 | 2.2 | 2.2 | 2.2 |
| pH | 9 | 9 | 9 | 9 |
| Hardness (Shore A) | 34 | 28 | 28 | 28 |
| TS (MPa) | 1.66 | 1.23 | 1.35 | 1.11 |
| EB (%) | 784 | 687 | 787 | 894 |
| 100% modulus (MPa) | 0.40 | 0.32 | 0.32 | 0.34 |
| Flow threshold (Pa) | 173 | 256 | 334 | — |
| Adhesiveness to: |  |  |  |  |
| glass: | x | xx | xx | xx |
| concrete: | x | xx | xx | xx |

EXAMPLES 14 TO 17 AND COMPARATIVE EXAMPLES 18 AND 19

Preparation of the mill base (A14):

The following materials were mixed under stirring:

(i) 909 parts of an α,ω-(dihydroxy)polydimethylsiloxane oil having a viscosity of 160 mPa.s at 25° C.;

(ii) 45.4 parts of the nonionic surfactant Cemulsol ® NP12 (polyethoxylated nonylphenol), marketed by Rhone-Poulenc;

(iii) 45.6 g of distilled water, added slowly over 15 minutes.

The mixture obtained was passed through the colloid mill and 1,000 parts of mill base were obtained.

Preparation of the emulsion E14:

To 500 parts of the mill base (A14) thus obtained were added 50 parts of a styrene/alkyl acrylate latex marketed by Rhone-Poulenc under the trademark Rhodopas ® DEA913 which had the following characteristics:

Film-forming at a temperature above 16° C.:
Solids content : 38%
Particle size : 0.05 μm pH=8.5
Brookfield viscosity (50 revolutions per minute): 250 mPa.s.

67 parts of water were then added and then, very rapidly, 79 parts of an aqueous solution containing 20% by weight of dodecylbenzenesulfonic acid (DBSA). Stirring was continued for 3 hours and the mixture was then permitted to polymerize while standing for an additional 21 hours. At the end of polymerization, it was neutralized with 15.9 parts of an aqueous solution containing 50% by weight of triethanolamine to obtain emulsion E14, whose final composition and characteristics are reported in Table 4 below.

Preparation of emulsion E15:

500 parts of mill base (A14) were diluted with 50 parts of Rhodopas ® DEA913 latex and then with 89 parts of an aqueous solution containing 14.83 by weight of sodium laurylsulfate and, finally, with 48.4 parts of distilled water. After stirring, 7.6 parts of an aqueous solution containing 22% by weight of hydrochloric acid (HCl) were introduced to initiate the polymerization.

After 24 hours of standing at 25° C., the mixture was neutralized with 13.7 g of triethanolamine at a concentration of 50% by weight in water. The final composition and the characteristics of the emulsion E15 thus obtained are reported in Table 4 below.

Preparation of emulsion E16:

The procedure was exactly the same as for preparing emulsion E15, except that:

(i) 100 parts of Rhodopas ® were added;
(ii) no distilled water was added.

Preparation of emulsion E17:

This was obtained by diluting emulsion (E16) with an appropriate amount of distilled water.

Preparation of emulsion E18:

The procedure for preparing emulsion (E14) was repeated, except that no latex was introduced.

Preparation of emulsion E19:

The procedure for preparing emulsion (E15) was repeated, except that no latex was introduced.

The compositions and the characteristics of emulsions E14 to E19 are reported in Table 4 below. Comparison of the solids contents and of the corresponding viscosities, measured with a Rheomat ® viscometer at 25° C. at a shear rate of 1 s$^{-1}$, illustrates the advantage of the twin-population emulsions E14 to E17, which made it possible to obtain high solids contents, typically desirable for applications in the construction industry, while preserving the low viscosity values which are compatible with the processes for preparing the filled final dispersion.

TABLE 4

| EXAMPLE | 14 | 15 | 16 | 17 | 18 | 19 |
|---|---|---|---|---|---|---|
| EMULSION | E14 | E15 | E16 | E17 | E18 | E19 |
| Compositions: parts by weight | | | | | | |
| Hydroxylated silicone oil | 652.2 | 641.3 | 641 | 596.5 | 636.9 | 637 |
| Cemulsol NP12 | 32.6 | 32 | 32 | 29.8 | 31.8 | 31.8 |
| Sodium laurylsulfate | — | 18.6 | 18.7 | 17.4 | — | 18.6 |
| DBSA | 22.8 | — | — | — | 22.3 | — |
| Pure HCl | — | 2.4 | 2.4 | 2.2 | — | 2.4 |
| Pure triethanolamine | 11.4 | 9.7 | 9.7 | 9.0 | 11.2 | 9.7 |
| Water | 253.8 | 225.5 | 155.2 | 213.8 | 297.8 | 300.5 |
| Rhodopas DEA913 latex | 27.2 | 70.5 | 141 | 131 | — | — |
| Characteristics: | | | | | | |
| Measured solids content (%) M.S.C. | 74.6 | 73.85 | 76.3 | 71 | 71 | 71.6 |
| Calculated solids content (%) C.S.C. | 73.0 | 73.1 | 75.8 | — | — | — |
| Viscosity of the silicone polymer (Pa.s) | 110 | 150 | 90 | 90 | 320 | 220 |
| Viscosity of the emulsion at 1 s$^{-1}$ (Pa.s) | 28 | 28 | 27 | 14.8 | 52 | 50 |
| M.S.C./emulsion viscosity ratio | 2.66 | 2.64 | 2.06 | 4.80 | 1.36 | 1.43 |

EXAMPLE 20 AND COMPARATIVE EXAMPLE 21

Formulation of filled aqueous dispersions D14 and D18:

Preparation of dispersion D14:

The following ingredients were added in this order to a 5-liter Meili ® type bladed kneader, an incorporation period of 10 minutes being observed each time a new ingredient was introduced:

(i) 134 parts of emulsion (E14);
(ii) 2 parts of an aqueous solution containing 50% by weight of potassium hydroxide;
(iii) 0.52 parts of an aqueous emulsion containing 37% by weight of di-n-octyltin dilaurate;
(iv) 100 parts of precipitated CaCO$_3$ having a mean particle size of 70 nonometers;
(v) 7 parts of the same hydroxylated silicone resin as that employed in Example 10.

The final mixture obtained was homogenized for an additional 30 minutes under a reduced pressure of 1.33 kPa.

The composition obtained was stored in an airtight cartridge and at room temperature for about 15 days. The mechanical properties were measured by following the procedure of Example 1, except that the film of elastomer was permitted to dry for 15 days.

The composition of D14 and its mechanical properties are reported in Table 5 below.

Preparation of dispersion (D18):

The procedure employed for (D14) was repeated exactly, except that 141 parts of emulsion (E18) were employed.

The composition of D18 and its mechanical properties are reported in Table 5 below.

From Table 5, it will be seen that an elastomer which had mechanical properties similar to those obtained from D18 was obtained with D14.

TABLE 5

| EXAMPLE | 20 | 21 |
|---|---|---|
| Composition (in parts by weight) | D14 | D18 |
| Emulsion D14 | 134 | — |
| Emulsion D18 | — | 141 |
| 50% KOH solution | 2 | 2 |
| Sn emulsion | 0.52 | 0.52 |
| CaCO$_3$ | 100 | 100 |
| Silicone resin | 7 | 7 |
| Pourability (Boeing test) in mm | 0 | 0 |
| Shore A hardness | 30 | 28 |
| TS (MPa) | 30 | 28 |
| EB (%) | 678 | 908 |
| 100% modulus (MPa) | 0.55 | 0.40 |

An emulsion (A) was prepared by polymerizing 1,000 g of an α,ω-(dihydroxy)polydimethylsiloxane oil having a viscosity of 100 mPa.s at 25° C. in the presence of 30 g of dodecylbenzenesulfonic acid and 50 g of Cemulsol ® 10/20, marketed by Rhone-Poulenc, which is a nonionic surfactant, namely, a compound polyoxyalkylenated with approximately 10 ethylene oxide units and 20 propylene oxide units.

The emulsion polymerization was terminated by neutralizing the catalyst with 14.5 g of triethanolamine when the oil viscosity reached 300,000 mPa.s at 25° C.

The emulsion (A) obtained had a solids content of 60%.

In the case of each additive, the following constituents were incorporated in 158 parts of emulsion (A), under stirring for 10 minutes:

(i) 7 parts of a nonfilm-forming polystyrene/-homopolymer latex which had the following characteristics:
  Solids content: : 50%
  pH: 8
  Viscosity at 25 ° C. ( 50 revolutions/min ): less than 100 mPa.s
  Particle diameter: ≃0.45 μm;
(ii) 2.2 parts of a 50% potassium hydroxide solution;
(iii) 7 parts of a hydroxylated silicone resin introduced as such, containing 2.2% by weight of hydroxyl groups, comprising 70% by weight of $CH_3SiO_{1.5}$ units and 30% by weight of $(CH_3)_2SiO$ units. This resin was soluble in toluene and had a molecular weight of approximately 1,300 and a $CH_3/Si$ molar ratio=1.77;
(iv) 2.6 parts of aqueous emulsion containing 37% by weight of di-n-octyltin dilaurate;
(v) 100 parts of precipitated $CaCO_3$ having a mean particle size of 70 nonometers.

The final mixture was homogenized for an additional 30 minutes at a reduced pressure of 1.33 kPa.

The final dispersion had a solids content of 75% and a pH of 8.5.

After 7 days of storage, the dispersion was spread with a doctor blade into a 2-mm thick film which was permitted to dry at room temperature (20° C.) for 10 days.

The following average mechanical properties were measured on a first batch of dried films:
  (a) Shore A hardness (SAH) according to ASTM Standard D-2240;
  (b) Tensile strength (TS) according to AFNOR Standard T-46 002 corresponding to ASTM Standard D 412, in MPa;
  (c) Elongation at break (EB) in % according to AFNOR Standard T 46 002;
  (d) Elasticity modulus (EM) at 100% elongation according to AFNOR Standard T 46 002, in MPa;
  (e) Flow threshold in Pa, measured in a Carrimed ® viscometer.

The mechanical properties obtained are reported in Table 6 below.

To assess adhesiveness, a 4-mm thick bead of aqueous dispersion was deposited onto a glass or concrete support. After 12 days, the adhesiveness of the elastomer formed was assessed by pulling the bead by hand.

The adhesions were qualified in three ways:
  (1) good adhesiveness when the bead could not be stripped from its support (indicated as + +);
  (2) average adhesiveness when the bead is stripped with difficulty and over small areas (indicated as +);
  (3) absence of adhesiveness when the bead is stripped easily (indicated as 0).

The assessments of adhesion are reported in Table 6 below.

COMPARATIVE EXAMPLE 23

The procedure of Example 1 was repeated exactly, except that the 7 parts of organic latex were not incorporated. The final dispersion had a solids content of 76% and a pH of 9.

The mechanical properties and the assessments of adhesion are reported in Table 6 below.

EXAMPLE 24

The procedure of Example 22 was repeated exactly, except that 20 parts of organic latex were incorporated. The final dispersion had a solids content of 74% and a pH of 9.

The mechanical properties and the assessments of the adhesion are reported in Table 6 below.

EXAMPLE 25

The operating procedure of Example 22 was repeated exactly, except that a nonfilm-forming polystyrene homopolymer latex was employed, marketed by Rhone-Poulenc under the trademark Rhodopas SO51 ®, which had the following characteristics:
  Solids content: : 50%
  pH : 8
  Brookfield viscosity at 23° C. (50 revolutions/min): 150 mPa.s
  Particle diameter: approximately 0.16 μm.

The results obtained are reported in Table 7 below.

EXAMPLES 26 AND 27

The procedure of Example 25 was repeated exactly, except that 20 and 40 parts of Rhodopas S051 ® organic latex were introduced, respectively.

The results obtained are reported in Table 7 below.

TABLE 6

|  | EXAMPLE 22 parts by weight | COMPARATIVE EXAMPLE 23 parts by weight | EXAMPLE 24 parts by weight |
|---|---|---|---|
| Emulsion (A) | 158 | 158 | 158 |
| Organic latex | 7 | 0 | 20 |
| Silicone resin | 7 | 7 | 7 |
| Dioctyltin dilaurate emulsion | 2.6 | 2.6 | 2.6 |
| Precipitated $CaCO_3$ ($\phi \simeq$ 70 nm) | 100 | 100 | 100 |
| KOH (50%) | 2.2 | 2.2 | 2.2 |
| pH | 9 | 9 | 9 |
| Hardress (Shore A) | 34 | 34 | 33 |
| TS (MPa) | 1.27 | 1.66 | 1.37 |
| EB (%) | 611 | 784 | 680 |
| 100% modulus (MPa) | 0.50 | 0.40 | 0.52 |
| Flow threshold (Pa) | 190 | 174 | 252 |
| Adhesiveness to: | | | |
| glass: | ++ | + | ++ |
| concrete: | ++ | + | ++ |

TABLE 7

|  | COMPARATIVE EXAMPLE 23 parts by weight | EXAMPLE 25 parts by weight | EXAMPLE 26 parts by weight | EXAMPLE 27 parts by weight |
|---|---|---|---|---|
| Emulsion (A) | 158 | 158 | 158 | 158 |
| Organic latex | 0 | 7 | 20 | 40 |
| Silicone resin | 7 | 7 | 7 | 7 |
| Dioctyltin dilaurate emulsion | 2.6 | 2.6 | 2.6 | 2.6 |
| Precipitated $CaCO_3$ ($\phi \simeq$ 70 nm) | 100 | 100 | 100 | 100 |
| KOH (50%) | 2.2 | 2.2 | 2.2 | 2.2 |
| pH | 9 | 9 | 9 | 9 |
| Hardness (Shore A) | 34 | 30 | 30 | 32 |
| TS (MPa) | 1.66 | 1.42 | 1.28 | 1.31 |
| EB (%) | 784 | 746 | 808 | 904 |
| 100% modulus (MPa) | 0.40 | 0.43 | 0.43 | 0.33 |
| Flow threshold (Pa) | 174 | 261 | 303 | — |

TABLE 7-continued

| | COMPARATIVE EXAMPLE 23 parts by weight | EXAMPLE 25 parts by weight | EXAMPLE 26 parts by weight | EXAMPLE 27 parts by weight |
|---|---|---|---|---|
| Adhesiveness to: | | | | |
| glass: | + | ++ | ++ | ++ |
| concrete: | + | ++ | ++ | ++ |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. An aqueous silicone dispersion crosslinkable into an elastomeric state on removal of water therefrom under ambient conditions, comprising (A) an oil-in-water base emulsion of an $\alpha,\omega$-(dihydroxy)polydiorganosiloxane stabilized with at least one anionic or nonionic surface-active agent, or mixture thereof, (B) an aqueous latex of an organic (co)polymer having a particle size ranging from 0.01 to 0.5 $\mu$m and a solids content ranging from 20% to 70% by weight, (C) an effective crosslinking amount of at least one crosslinking agent for reacting with the emulsion (A) to produce an elastomeric state, and (D) at least one nonsiliceous filler material in an amount effective for semi-reinforcement or packing, said aqueous dispersion having a solids content of at least 40% by weight.

2. The aqueous silicone dispersion as defined by claim 1, further comprising (E) a catalytically effective amount of a metal curing catalyst.

3. The aqueous silicone dispersion as defined by claim 1, comprising 100 parts by weight of said stabilized oil-in-water emulsion (A), from 2 to 80 parts by weight of said aqueous latex (B), and from 5 to 200 parts by weight of said at least one nonsiliceous filler material (D).

4. The aqueous silicone dispersion as defined by claim 3, comprising from 3 to 40 parts by weight of said aqueous latex (B), and from 50 to 150 parts by weight of said at least one nonsiliceous filler material (D).

5. The aqueous silicone dispersion as defined by claim 3, further comprising from 0.01 to 3 parts by weight of a metal curing catalyst (E).

6. The aqueous silicone dispersion as defined by claim 1, wherein said aqueous latex of organic (co)polymer (B) comprises a (co)polymerizate of at least one (a) alkyl (meth)acrylate, (b) $\alpha,\beta$-ethylenically unsaturated ester of a monocarboxylic acid, the acid moiety of which is not polymerizable, (c) ester or half-ester of an $\alpha,\beta$-ethylenically unsaturated polycarboxylic acid, (d) vinyl halide, (e) vinylaromatic, (f) conjugated aliphatic diene, or (g) $\alpha,\beta$-ethylenically unsaturated nitrile monomer.

7. The aqueous silicone dispersion as defined by claim 6, said aqueous latex (B) comprising a styrene/alkyl acrylate copolymer in which the styrene/acrylate weight ratio ranges from 30/70 to 70/30, a polyvinyl acetate homopolymer or a polystyrene homopolymer.

8. The aqueous silicone dispersion as defined by claim 3, said at least one crosslinking agent (C) comprising colloidal silica, an organosiliconate, sodium silicate, a pyrogenic or precipitated silica powder, a silsesquioxane resin, a reactive silicone resin which comprises alkoxy and acyloxy functional groups, a silicone resin, Which is insoluble in toluene, an hydroxylated silicone resin containing, per molecule, at least 2 different structural units selected from among those of the formulae: $R_3SiO_{0.5}$, $R_2SiO$, $RSiO_{1.5}$ and $SiO_2$, in which R is a $C_1$–$C_6$ alkyl, vinyl or 3,3,3-trifluoropropyl radical and has a weight content of hydroxyl groups of from 0.1% to 10%, a silane of the formula:

$$R_aSiX_{4-a}$$

in which R is a monovalent organic radical, a is 1 or 0, X is a condensable or hydrolyzable alkoxy, acyloxy, ketiminoxy, alkylamino, amido or alkenyloxy group, or mixture thereof.

9. The aqueous silicone dispersion as defined by claim 3, said oil-in-water emulsion (A) having a solids content of at least 40% by weight.

10. The aqueous silicone dispersion as defined by claim 3, said at least one nonsiliceous filler material (D) comprising calcium carbonate, carbon black, titanium dioxide, aluminum oxide, hydrated alumina, expanded vermiculite, hydrated borax, unexpanded vermiculite, zinc oxide, mica, talc, iron oxide, barium sulfate, slaked lime, or mixture thereof.

11. The aqueous silicone dispersion as defined by claim 10, said at least one nonsiliceous filler material (D) comprising precipitated calcium carbonate having a mean particle diameter of less than 0.1 $\mu$m.

12. The aqueous silicone dispersion as defined by claim 5, said metal curing catalyst (E) comprising an aqueous emulsion of an organotin salt.

13. The aqueous silicone dispersion as defined by claim 3, film-forming under ambient conditions.

14. The aqueous silicone dispersion as defined by claim 3, nonfilm-forming under ambient conditions.

15. The aqueous silicone dispersion as defined by claim 8, said at least one crosslinking agent (C) comprising the silane of the formula $R_aSiX_{4-a}$, wherein R is methyl or vinyl.

16. The aqueous silicone dispersion as defined by claim 1, said at least one anionic or nonionic surface-active agent stabilizing said oil-in-water emulsion (A) comprising a salt of a sulfonic acid, or a polyoxyethylenated alkylphenol.

17. The aqueous silicone dispersion as defined by claim 1, having a solids content ranging from about 60% to about 90%.

18. The aqueous silicone dispersion as defined by claim 1, having a pH of from 8 to 13.

19. The aqueous silicone dispersion as defined by claim in dehydrated, crosslinked elastomeric state.

20. The aqueous silicone dispersion as defined by claim 1, further comprising (F) a siliceous additive in an amount effective to impart thixotropic properties to the emulsion.

21. The aqueous silicone dispersion defined by claim 20 wherein said siliceous additive (F) comprises colloidal silica, pyrogenic silica, precipitated silica, diatomaceous earth, ground quartz or mixture thereof.

22. An aqueous silicone dispersion crosslinkable into an elastomeric state on removal of water therefrom under ambient conditions, comprising (A) an oil-in-water base emulsion of an $\alpha,\omega$-(dihydroxy)polydiorganosiloxane stabilized with at least one anionic or nonionic surface-active agent, or mixture thereof, (B) an aqueous latex of an organic (co)polymer having a particle size ranging from 0.01 to 0.5 μm and a solids content ranging from 20% to 70% by weight, (C) an effective crosslinking amount of at least one crosslinking agent, and (D) at least one nonsiliceous filler material in an amount effective for semi-reinforcement or packing, wherein the crosslinking agent (C) reacts with the emulsion (A) to produce an elastomeric state and wherein said organic (co)polymer of said aqueous latex (B) does not polycondense with said polydiorganosiloxane polymer in said oil-in-water emulsion (A), said aqueous dispersion having a solids content of at least 40% by weight.

23. An aqueous silicone dispersion cross-linkable into an elastomeric state on removal of water therefrom under ambient conditions, comprising: (A) an oil-in-water base emulsion of an α,ω-(dihydroxy) polydiorganosiloxane stabilized with at least one anionic or nonionic surface-active agent, or mixture thereof; (B) an aqueous latex of an organic (co)polymer having a particle size ranging from 0.01 to 0.5 μm and a solids content ranging from 20% to 70% by weight; (C) an effective crosslinking amount of at least one crosslinking agent; and (D) at least one non-siliceous filler material in an amount effective for semi-reinforcement or packing, wherein the dispersion has (i) a first population of particles originating from the aqueous latex (B) having a particle size ranging from about 0.01 μm to about 0.15 μm and (ii) a second population of particles originating from the oil-in-water emulsion (A) having a particle size ranging from 0.15 μm to 100 μm.

24. The aqueous silicone dispersion as defined by claim 23, wherein the dispersion has (iii) a solids content of more than 60% by weight, and (iv) a viscosity of less than 50,000 in Pa.s at 25° C., measured at a shear rate of 1 s$^{-1}$ prior to incorporation of the nonsiliceous filler material.

25. The aqueous silicone dispersion as defined by claim 24, wherein said aqueous latex (B) has a solids content of from about 20% to 40% by weight.

* * * * *